(12) United States Patent
Cornwall et al.

(10) Patent No.: US 7,772,403 B2
(45) Date of Patent: Aug. 10, 2010

(54) PROCESS TO PREPARE SULFONYL CHLORIDE DERIVATIVES

(75) Inventors: Philip Cornwall, Loughborough (GB); Daniel Horner, Loughborough (GB)

(73) Assignee: AstraZeneca AB (SE)

(*) Notice: Subject to any disclaimer, the term of this patent is extended or adjusted under 35 U.S.C. 154(b) by 0 days.

(21) Appl. No.: 12/282,971

(22) PCT Filed: Mar. 15, 2007

(86) PCT No.: PCT/SE2007/000255

§ 371 (c)(1),
(2), (4) Date: Sep. 15, 2008

(87) PCT Pub. No.: WO2007/106021

PCT Pub. Date: Sep. 20, 2007

(65) Prior Publication Data

US 2009/0054659 A1    Feb. 26, 2009

(51) Int. Cl.
A61K 31/4166 (2006.01)
C07D 233/72 (2006.01)

(52) U.S. Cl. .................................. 548/317.1; 514/389
(58) Field of Classification Search ............ 548/317.1; 514/389

See application file for complete search history.

(56) References Cited

U.S. PATENT DOCUMENTS

| | | | |
|---|---|---|---|
| 3,529,019 A | 9/1970 | Suh et. al. | |
| 7,132,434 B2 | 11/2006 | Eriksson et al. | |
| 7,354,940 B2 | 4/2008 | Henriksson et al. | |
| 7,368,465 B2 | 5/2008 | Eriksson et al. | |
| 7,427,631 B2 | 9/2008 | Eriksson et al. | |
| 2003/0130273 A1 | 7/2003 | Sheppeck et al. | |
| 2004/0106659 A1 | 6/2004 | Rosenschold | |
| 2004/0110809 A1 | 6/2004 | Lepisto et al. | |
| 2004/0116486 A1 | 6/2004 | Lepisto et al. | |
| 2004/0138276 A1 | 7/2004 | Eriksson et al. | |
| 2004/0147573 A1 | 7/2004 | Eriksson et al. | |
| 2005/0026990 A1 | 2/2005 | Eriksson et al. | |
| 2005/0245586 A1 | 11/2005 | Henriksson et al. | |
| 2005/0256176 A1 | 11/2005 | Burrows et al. | |
| 2006/0063818 A1 | 3/2006 | Burrows et al. | |
| 2006/0276524 A1 | 12/2006 | Henriksson et al. | |
| 2008/0004317 A1 | 1/2008 | Gabos et al. | |
| 2008/0032997 A1 | 2/2008 | Gabos et al. | |
| 2008/0064710 A1 | 3/2008 | Gabos et al. | |
| 2008/0171882 A1 | 7/2008 | Eriksson et al. | |
| 2008/0221139 A1 | 9/2008 | Chapman et al. | |
| 2008/0262045 A1 | 10/2008 | Eriksson et al. | |
| 2008/0293743 A1 | 11/2008 | Gabos et al. | |
| 2008/0306065 A1 | 12/2008 | Eriksson et al. | |

FOREIGN PATENT DOCUMENTS

| WO | WO 00/09103 | 2/2000 | |
|---|---|---|---|
| WO | WO 02/074748 | 9/2002 | |
| WO | WO 02/074749 | 9/2002 | |
| WO | WO 02/074750 | 9/2002 | |
| WO | WO 02/074751 | 9/2002 | |
| WO | WO 02/074752 | 9/2002 | |
| WO | WO 02/074767 | * 9/2002 | |
| WO | WO 02/096426 | 12/2002 | |
| WO | WO 03/040098 | 5/2003 | |
| WO | WO 03/087057 | 10/2003 | |
| WO | WO 2004/020415 | 3/2004 | |
| WO | WO 2004/024698 | 3/2004 | |
| WO | WO 2004/024718 | 3/2004 | |
| WO | WO 2004/024721 | 3/2004 | |
| WO | WO 2006/004532 | 1/2006 | |
| WO | WO 2006/004533 | 1/2006 | |
| WO | WO 2006/065215 | 6/2006 | |
| WO | WO 2006/065216 | 6/2006 | |
| WO | WO 2006/077387 | 7/2006 | |
| WO | WO 2007/106021 | 9/2007 | |
| WO | WO 2007/106022 | 9/2007 | |

OTHER PUBLICATIONS

Griffith "Cysteinesulfinate Metabolism: Altered partitioning between transamination and decarboxylation following administration of β-methyleneaspartate" J. Biol. Chem. 1983 (258) 1591-1598.

Lora-Tamayo et al. "Anticancerousos Potenciales." An. Quim. 1968 (64) 591-606.

Mosher "Potential Anticancer Agents. VI. Synthesis of α-Amino-γ-sulfamoylbutyric Acids with Substituents on the Sulfonamide Nitrogen" J. Org. Chem. 1958 (23) 1257-1261.

Smith, Michael B., Organic Synthesis Second Edition, 3.9.A Oxidation of sulfur compounds, McGraw-Hill 2002, ISBN-0-07-048242-X, p. 280.

(Continued)

Primary Examiner—Kamal A Saeed
Assistant Examiner—Janet L Coppins
(74) Attorney, Agent, or Firm—Fish & Richardson P.C.

(57) ABSTRACT

A novel process for the preparation of hydantoin sulfonyl chlorides of general formula (I) wherein R and n are as specified in the description, and certain novel intermediates thereto, are disclosed.

(I)

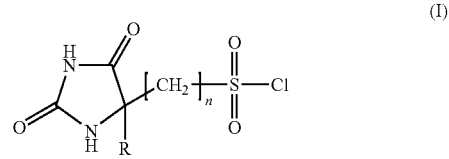

11 Claims, No Drawings

OTHER PUBLICATIONS

STN International, File CAPLUS, CAPLUS accession No. 1968:506154, Doc. No. 69:106154, Lora-Tamayo, J. et al. "Potential anticancer agents, VI. Sulfonic analogs of aspartic acid" & An. Quim. 1968 (64) 591-606.

Whittaker et al. "Design and Therapeutic Application of Matrix Metalloproteinase Inhibitors." Chem Rev. 1999 (99) 2735-2776.

USPTO Non-Final Office Action in U.S. Appl. No. 11/928,040, mailed Dec. 5, 2008, 16 pages.

Fish & Richardson P.C., Amendment in Reply to Action of Dec. 5, 2008 in U.S. Appl. No. 11/928,040, filed May 5, 2009, 12 pages.

USPTO Notice of Allowance in U.S. Appl. No. 11/928,040, mailed Jul. 14, 2009, 10 pages.

* cited by examiner

PROCESS TO PREPARE SULFONYL CHLORIDE DERIVATIVES

CROSS-REFERENCE TO RELATED APPLICATIONS

This application is a national phase application under 35 U.S.C. §371 of PCT International Application No. PCT/SE2007/000255, filed Mar. 15, 2007, which claims the benefit of U.S. Provisional Application No. 60/782,892, filed Mar. 16, 2006. Each of these prior applications is incorporated herein by reference in its entirety.

FIELD OF THE INVENTION

The present invention discloses a novel process for the preparation of hydantoin sulfonyl chlorides. Certain novel intermediates are also disclosed.

BACKGROUND OF THE INVENTION

Mosher et al, J. Org. Chem., 1958, 23, 1257-1261 describe the synthesis of DL-5-(β-chlorosulfonylethyl)hydantoin and L-5-(chlorosulfonylmethyl)hydantoin by the chlorination in aqueous media of DL-homocystine hydantoin and L-cystine hydantoin respectively.

WO 02/074767, WO 2004/024698 and WO 2006/065215 disclose classes of hydantoin-containing metalloproteinase inhibitors that are useful in therapy. Key intermediates useful in the synthesis of certain of the compounds disclosed in WO 02/074767, WO 2004/024698 and WO 2006/065215 are sulfonyl chlorides of general formula:

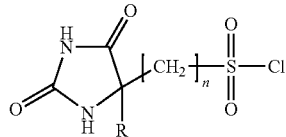

Specific sulfonyl chlorides that are disclosed in WO 02/074767 and/or WO 2004/024698 and/or WO 2006/065215 are:
(RS)-2-(2,5-dioxo-4-imidazolidinyl)-1-ethanesulfonyl chloride;
(R)-(2,5-dioxo-4-imidazolidinyl)methanesulfonyl chloride;
(S)-(2,5-dioxo-4-imidazolidinyl)methanesulfonyl chloride;
(RS)-(4-methyl-2,5-dioxo-4-imidazolidinyl)methanesulfonyl chloride;
(RS)-(4-ethyl-2,5-dioxo-4-imidazolidinyl)methanesulfonyl chloride;
(RS)-(4-methyl-2,5-dioxo-4-imidazolidinyl)ethanesulfonyl chloride;
(RS)-(4-ethyl-2,5-dioxo-4-imidazolidinyl)ethanesulfonyl chloride;
(4S)-(4-methyl-2,5-dioxo-4-imidazolidinyl)methanesulfonyl chloride;
(4R)-(4-methyl-2,5-dioxo-4-imidazolidinyl)methanesulfonyl chloride;
(4S)-(4-ethyl-2,5-dioxo-4-imidazolidinyl)methanesulfonyl chloride; and
(4S)-(4-cyclopropyl-2,5-dioxoimidazolidin-4-yl)methanesulfonyl chloride.

The sulfonyl chlorides specifically disclosed in WO 02/074767, WO 2004/024698 and WO 2006/065215 were prepared either by:

(i) chlorination in aqueous media of the corresponding disulfide derivative essentially as described by Mosher; or
(ii) by analogous chlorination in aqueous media of the corresponding benzylsulphide derivative.

We now disclose an alternative and improved process for the synthesis of hydantoin-containing sulfonyl chlorides of the above type.

DISCLOSURE OF THE INVENTION

According to the present invention we disclose a process for the preparation of sulfonyl chloride derivatives of general formula (I)

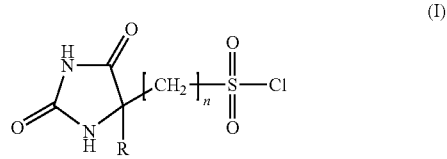

wherein

R represents C1 to 4 alkyl or C3 to 5 cycloalkyl; and n represents an integer 1 or 2;

which process involves reaction of a compound of formula (II)

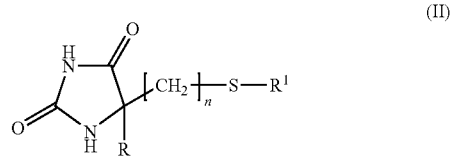

wherein $R^1$ represents $Bu^t$, $PhCH_2$, $Ph_2CH$, $Ph_3C$ or C1 to 6 alkanoyl; and R and n are as defined in formula (I);

with hydrogen peroxide, followed by chlorination in an aqueous media.

The hydrogen peroxide is generally used as an aqueous solution. Conveniently, as a 35% w/w solution in water. Typically, 0.95 to 1.05 equivalents of hydrogen peroxide are used, particularly about 1.0 equivalents. However, larger amounts of hydrogen peroxide may be used.

Chlorination is generally performed using chlorine gas. Generally chlorine gas is passed into the rapidly stirred reaction mixture until the solution develops a persistent green colouration which indicates completion of the reaction. At the same time a slight drop in temperature is typically also observed. Typically, 2.0 to 2.8 equivalents of chlorine are used.

Preferably the oxidation with hydrogen peroxide and the chlorination reaction are carried out as sequential steps within a single reaction vessel.

In one preferred embodiment, $R^1$ represents $Bu^t$.
In another preferred embodiment, $R^1$ represents $PhCH_2$.
In another embodiment, n represents the integer 1.
In another preferred embodiment, R represents $CH_3$.

In another embodiment, R represents $CH_3CH_2$.

In another embodiment, R represents cyclopropyl.

In one embodiment, $R^1$ represents $Bu^t$, n represents the integer 1 and R represents $CH_3$ or $CH_3CH_2$ or cyclopropyl.

In another embodiment, $R^1$ represents $PhCH_2$, n represents the integer 1 and R represents $CH_3$ or $CH_3CH_2$ or cyclopropyl.

The process is carried out in a solvent such as aqueous acetic acid or in a mixture of water and a suitable inert solvent such as chloroform or dichloromethane or in a mixture of water and a suitable inert solvent additionally comprising acetic acid.

In one embodiment, the process is carried out in acetic acid containing by volume 5 to 15% water. In another embodiment, the process is carried out in acetic acid containing 10 to 12% water. In another embodiment, the process is carried out in acetic acid containing about 11% water, specifically a mixture of acetic acid and water in a ratio of 8:1 by volume.

The process is carried out at a suitable temperature such as between −10° C. and +40° C., particularly between 0° C. and +20° C. The skilled man will appreciate that both steps in the process are potentially exothermic and therefore, depending on the scale on which the process is being carried out, some temperature variation is to be expected.

When compared to processes known in the prior art, the novel process of the present invention has the major environmental advantage that significantly lesser equivalents of chlorine are required in the chlorination step. There is thus a significant reduction in the emission of hydrogen chloride. The chlorination step of the present invention typically involves the use of about 2.0 to 2.8 equivalents of chlorine gas. In contrast, the prior art process involving direct chlorination of a sulphide derivative of formula (II) (without prior oxidation) typically involves the use of about 3.1 to 3.8 equivalents of chlorine gas.

Another major disadvantage of the prior art processes involving direct chlorination of a sulphide or disulfide derivative, particularly for large scale work, is that, depending on the exact nature of the group $R^1$, the sulfonyl chloride product (I) can be contaminated with varying amounts of the corresponding sulfonic acid derivative (III) wherein R and n are as defined above.

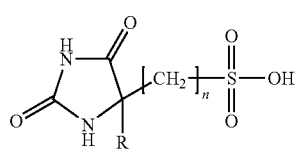

(III)

Thus, in the case of direct chlorination of the compound of formula (II) wherein $R^1$ is $PhCH_2$, the sulfonyl chloride of formula (I) is obtained in satisfactory yield and purity; but direct chlorination of the compound of formula (II) wherein $R^1$ is $Bu^t$ gives the sulfonyl chloride product (I) contaminated by 5% or more of the corresponding sulfonic acid derivative of general formula (III). Whilst such contaminated products are generally acceptable for routine laboratory work, they are not acceptable for large scale manufacturing processes.

The novel process of the present invention has the advantage that the reaction is less sensitive to the nature of the group $R^1$. Thus, compounds of formula (II) wherein $R^1$ is $PhCH_2$ or $R^1$ is $Bu^t$ both afford the required sulfonyl chloride (I) in excellent yield and purity.

Whilst not wishing to be restricted by theory, it is believed that the novel process of the present invention proceeds via the intermediacy of a sulfoxide of general formula (IV).

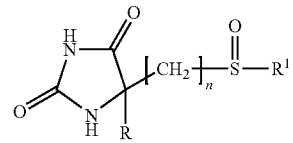

(IV)

Novel sulfoxides of general formula (IV), wherein R, $R^1$ and n are as defined above, useful as intermediates in the synthesis of sulfonyl chlorides of general formula (I), form another aspect of the present invention. In particular, novel sulfoxides of general formula (IV) wherein $R^1$ represents $Bu^t$ or $PhCH_2$; n represents the integer 1; and R represents $CH_3$ or $CH_3CH_2$ or cyclopropyl are claimed.

Again whilst not wishing to be restricted by theory, it is believed that the chlorination of the sulfoxide intermediate (IV) to give the sulfonyl chloride (I) may proceed, to a greater or lesser extent, via a sulfinic acid derivative of formula (V).

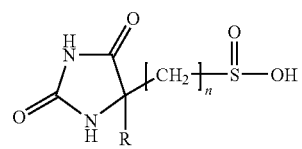

(V)

Novel sulfinic acid derivatives of formula (V), wherein R and n are as defined above, useful as intermediates in the synthesis of sulfonyl chlorides of general formula (I), form another aspect of the invention. In particular, novel sulfinic acid derivatives of general formula (V) wherein n represents the integer 1 and R represents $CH_3$ or $CH_3CH_2$ or cyclopropyl are claimed.

The compounds of formula (I), (I), (III), (IV) and (V) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Where optical isomers exist in the compounds of the invention, we disclose all individual optically active forms and combinations of these as individual specific embodiments of the invention, as well as their corresponding racemates.

The process proceeds satisfactorily irrespective of the optical form of the starting material or of any intermediates, such as the potentially chiral sulfoxides of general formula (IV).

Particular aspects of the invention are illustrated by the following Examples.

General Methods $^1$H NMR spectra were recorded on a Varian Unity 400 MHz or a Varian Unity Inova 500 MHz instrument. The central peaks of tetrahydrofuran-$d_8$ ($\delta_H$ 3.58 ppm) and dimethylsulfoxide-$d_6$ ($\delta_H$ 2.49 ppm), were used as internal references. Infra red spectra were recorded on a Perkin Elmer Spectrum FT-IR Spectrophotometer with Golden Gate accessory.

Unless stated otherwise, starting materials were commercially available. All solvents and commercial reagents were of laboratory grade and were used as received. The following method was used for LC purity and LC/MS analysis:

| Instrument: | Hewlett Packard 1100 series HPLC fitted with a diode array detector. |
|---|---|
| Column: | Metachem Polaris C18 3 μm × 150 mm × 3 mm |
| Mobile Phases: | A: 0.05% TFA |
| | B: 0.04% TFA in acetonitrile |
| Sample diluent: | Acetonitrile |
| Oven temperature: | 45° C. |
| Flow rate: | 0.42 ml/minute |
| Detection: | 220 nm |
| Injection volume: | 1 μl |
| Gradient: | Time    % B |
| | 0         5 |
| | 20       90 |
| Post time: | 5 minutes |
| Run time: | 20 minutes |

The following method was used to determine enantiomeric purity:

| Instrument: | Hewlett Packard 1100 series HPLC fitted with a diode array detector. |
|---|---|
| Column: | Astec Chirobiotic V 50 mm × 4.6 mm |
| Mobile Phases: | 70:30 isohexane:ethanol |
| Sample diluent: | Acetonitrile |
| Oven temperature: | 55° C. |
| Flow rate: | 3.0 ml/minute |
| Detection: | 210 nm |
| Injection volume: | 10 μl |
| Run time: | 5 minutes |

ABBREVIATIONS

But tertiary-butyl

DMSO dimethyl sulfoxide eq equivalent

STP standard temperature and pressure

THF tetrahydrofuran

TFA trifluoroacetic acid

EXAMPLE 1

[(4S)-4-Methyl-2,5-dioxoimidazolidin-4-yl]methanesulfonyl Chloride (from (5S)-5-[(benzylthio)methyl]-5-methylimidazolidine-2,4-dione

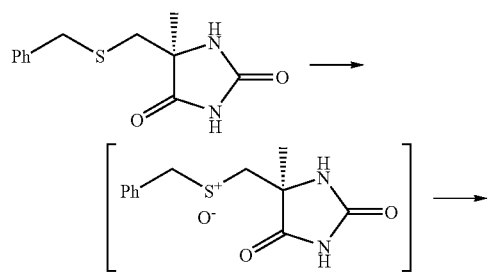

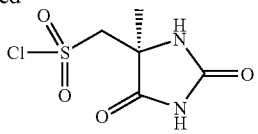

(5S)-5-[(Benzylthio)methyl]-5-methylimidazolidine-2,4-dione (WO 02/074767) (1.00 eq, 61.1 mmol, 15.3 g) was charged to a 250 mL jacketed vessel equipped with a mechanical stirrer. Acetic acid (2.14 mol, 122 mL, 128 g) was then added, and the mixture stirred at 300 rpm for 21 min. Water (849 mmol, 15.3 mL, 15.3 g) was added and the resulting solution cooled to 9° C. With the jacket temperature set at 10° C., a solution of hydrogen peroxide, 11.68M, 35% w/w in water (61.1 mmol, 5.23 mL, 5.94 g) was added as one charge. Twelve minutes after the addition of peroxide, the temperature of the mixture had risen to 11.4° C. The mixture was then stirred at 9 to 10° C. for 17 h. Analysis of the mixture by hplc revealed almost complete conversion to a pair of diastereoisomeric sulfoxides (less than 3% area of the S-benzyl starting material remaining). The mixture was stirred at 9 to 10° C. for 6 h, then cooled to 5 to 6° C. The stirrer speed was increased to 400 rpm and chlorine gas (10.5 g, 148 mmol, 3.32 L at STP) was passed into the mixture over 55 min. The temperature of the mixture rose to a maximum of 10° C. The end of reaction was indicated by a persistent green colouration of the mixture and a fall in temperature from 9 to 8° C. over 1 min. HPLC analysis of the mixture at this point revealed complete conversion of the sulfoxide intermediates. The mixture was heated to 15° C. and stirred for 23 h at 15° C., then heated to 35° C. to dissolve suspended solids, then discharged. The mixture was evaporated under reduced pressure to about 25% of the original volume. The temperature of the water bath was kept below 55° C. Toluene (718 mmol, 76.5 mL, 66.2 g) was charged to the residue and the mixture re-evaporated to low volume. Further toluene (718 mmol, 76.5 mL, 66.2 g) was charged and the mixture re-evaporated. Iso-hexane (577 mmol, 76.5 mL, 49.7 g) was charged to the residue to give a solid suspension that was collected by filtration. The filtration was fast resulting in the collection of large crystals on the filter. The crystals were washed with iso-hexane (231 mmol, 30.6 mL, 19.9 g) and sucked dry on the filter, to yield 16.32 g of solvent-damp solid. The product was dried in vacuo at 40° C. for 72 h to yield [(4S)-4-methyl-2,5-dioxoimidazolidin-4-yl]methanesulfonyl chloride as a white solid (0.967 eq, 59.1 mmol, 13.4 g) in 97% yield.

$^1$H NMR (399.98 MHz, THF-D8) δ 9.91 (s, 1H), 7.57 (s, 1H), 4.53 (d, J=14.6 Hz, 1H), 4.44 (d, J=14.6 Hz, 1H), 1.52 (s, 3H).

FTIR (Neat) 3192, 3072, 1704, 1408, 1369, 1287, 1165, 875, 762 cm$^{-1}$.

HPLC analysis (area %) indicated a purity of 98.30% with the corresponding sulfonic acid at 1.42%.

EXAMPLE 2

[(4S)-4-Methyl-2,5-dioxoimidazolidin-4-yl]methanesulfonyl Chloride (from (5S)-5-[(tert-butylthio)methyl]-5-methylimidazolidine-2,4-dione

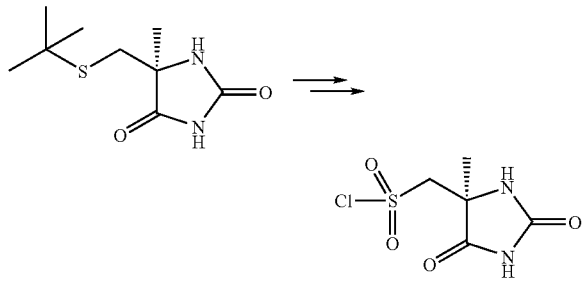

(5S)-5-[(Tert-butylthio)methyl]-5-methylimidazolidine-2,4-dione (WO 03/106689) (1.00 eq, 56.9 mmol, 12.3 g) was charged to a 250 mL jacketed vessel followed by acetic acid (1.72 mol, 98.4 mL, 103 g) and water (683 mmol, 12.3 mL, 12.3 g). The resulting mixture was stirred at 300 rpm and heated to 35° C. to dissolve all solids. The mixture was cooled to 10° C. and a solution of hydrogen peroxide, 11.68M, 35% w/w in water (56.9 mmol, 4.87 mL, 5.53 g) was charged as one portion, resulting in an exotherm to 17° C. Analysis of the reaction mixture by hplc 48 min after the addition of peroxide revealed conversion to a diastereoisomeric mixture of sulfoxides along with 4.6 area % of starting material remaining. The mixture was cooled to 6° C., stirred at 400 rpm and chlorine gas (159 mmol, 3.57 L at STP, 2.80 eq) was added over 28 min (constant jacket temperature of 6° C.) until the reaction mixture turned green and a sharp decrease in temperature of the reaction mixture was noted. HPLC analysis of the mixture at this point revealed complete conversion of the sulfoxide intermediates to the required sulfonyl chloride. The mixture was heated to 15° C., discharged from the vessel and concentrated to about 30% of the original volume under reduced pressure. Toluene (577 mmol, 61.5 mL, 53.2 g) was then charged to give a 3 phase mixture, which was re-evaporated. Further toluene (798 mmol, 85.0 mL, 73.5 g) was added and the mixture re-evaporated. Iso-hexane (464 mmol, 61.5 mL, 40.0 g) was then added to the sticky residue to give a suspension that was collected by filtration, washed with iso-hexane (371 mmol, 49.2 mL, 32.0 g) and sucked dry on the filter. The damp product (16.27 g) was dried in a vacuum oven at 40° C. to give [(4S)-4-methyl-2,5-dioxoimidazolidin-4-yl]methanesulfonyl chloride as a white crystalline solid (0.868 eq, 49.4 mmol, 11.2 g) in 87% yield.

$^1$H NMR (399.98 MHz, THF-D8) δ 9.91 (s, 1H), 7.57 (s, 1H), 4.53 (d, J=14.6 Hz, 1H), 4.44 (d, J=14.4 Hz, 1H), 1.52 (s, 3H).

FTIR (Neat) 3191, 3072, 1704, 1409, 1369, 1287, 1166, 875, 762 cm$^{-1}$.

HPLC analysis (area %) indicated that the title compound had a purity of 99.63% containing [(4S)-4-methyl-2,5-dioxoimidazolidin-4-yl]methanesulfonic acid 0.37 area %.

The intermediacy of [(4S)-4-methyl-2,5-dioxoimidazolidin-4-yl]methanesulfinic acid was confirmed by LC/MS analysis of a sample of the reaction mixture taken 17 min after the start of the chlorine addition: m/z 193 (MH)$^+$, 210 (M+NH$_4$)$^+$, 385 (2M+H)$^+$, 407 (2M+Na)$^+$.

EXAMPLE 3

[(4S)-4-Methyl-2,5-dioxoimidazolidin-4-yl]methanesulfonyl Chloride (by direct chlorination of (5S)-5-[(tert-butylthio)methyl]-5-methylimidazolidine-2,4-dione without prior oxidation)

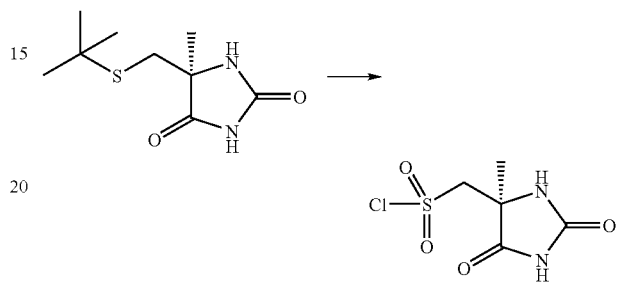

(5S)-5-[(Tert-butylthio)methyl]-5-methylimidazolidine-2,4-dione (1.00 eq, 83.7 mmol, 18.1 g) was charged to a jacketed vessel, followed by acetic acid (2.53 mol, 145 mL, 152 g) and water (1.00 mol, 18.1 mL, 18.1 g). Stirring was commenced (300 rpm) and the mixture heated to 30° C. to completely dissolve the solids. A nitrogen purge was then applied and the vessel contents cooled to approximately 4° C. The nitrogen flow was stopped, the vessel was sealed, and chlorine gas was bubbled into the mixture over 35 min (T$_{max}$ 13.8° C.). A green colouration developed and the chlorine supply was shut off. The green colouration discharged after several seconds indicating that the reaction was not complete and the addition of chlorine was resumed for 5 min resulting in an exotherm from 11.6° C. to 13.3° C. The green colour persisted after shutting off the chlorine supply indicating that end of reaction had been reached. Total amount of chlorine used was 21.6 g (305 mmol, 6.82 L at STP). The vessel was vented to the atmosphere, purged with nitrogen and heated to 15° C. HPLC analysis of the reaction mixture revealed complete consumption of starting material, the formation of the expected product and a significant amount (10 area %) of another by-product. The mixture was discharged, allowed to warm to ambient temperature and then evaporated to low volume. Toluene (850 mmol, 90.5 mL, 78.3 g) was charged to the mixture which was then re-evaporated. The toluene addition/re-evaporation procedure was repeated, then iso-hexane (683 mmol, 90.5 mL, 58.8 g) was charged to the residue. The mixture was set aside then later filtered. The collected crystals were washed with iso-hexane (273 mmol, 36.2 mL, 23.5 g) and sucked dry on the filter to give 20.79 g of damp product. The product was further dried at 40° C. in vacuo for approx 21 h to give [(4S)-4-methyl-2,5-dioxoimidazolidin-4-yl]methanesulfonyl chloride as a white solid (0.963 eq, 80.6 mmol, 18.3 g) in 96% yield, 93.80 area % purity by hplc.

$^1$H NMR (399.98 MHz, THF-D8) δ 9.92 (s, 1H), 7.58 (s, 1H), 4.53 (d, J=14.6 Hz, 1H), 4.44 (d, J=14.6 Hz, 1H), 1.52 (s, 3H);

containing [(4S)-4-methyl-2,5-dioxoimidazolidin-4-yl]methanesulfonic acid 6.20 area % by hplc:

$^1$H NMR (399.98 MHz, THF-D8) δ 9.66 (s, 1H), 7.21 (s, 1H), 3.45 (d, J=14.6 Hz, 1H), 3.37 (d, J=14.9 Hz, 1H), 1.46 (s, 3H).

EXAMPLE 4

[(4S)-4-methyl-2,5-dioxoimidazolidin-4-yl]methanesulfonyl chloride with isolation of the intermediate (5S)-5-[(tert-butylsulfinyl)methyl]-5-methylimidazolidine-2,4-dione

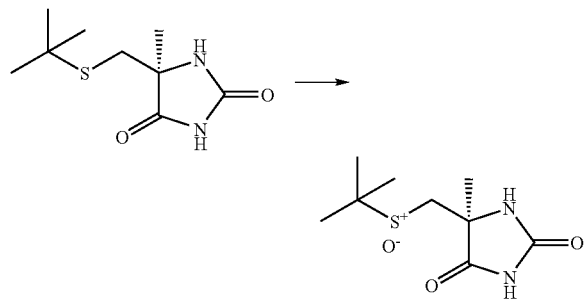

(5S)-5-[(Tert-butylthio)methyl]-5-methylimidazolidine-2,4-dione (1.00 eq, 46.2 mmol, 10.0 g) was charged to a vessel followed by methanol (2.64 mol, 107 mL, 84.5 g). The resulting clear solution was stirred and a solution of sulfuric acid, 4.40% w/w in iso-propanol (6.22 mmol, 13.9 mL, 13.9 g) was added. To this mixture was then added a solution of hydrogen peroxide, 11.68M, 35% w/w in water (107 mmol, 9.13 mL, 10.4 g) in one portion without external cooling (an exotherm from 22° C. to 41° C. over 10 min was noted). Hplc analysis of the reaction mixture approximately 1.5 h after the addition of the hydrogen peroxide revealed complete consumption of the starting material and the appearance of two new peaks (diastereoisomeric sulfoxides). The mixture was diluted with saturated aqueous sodium chloride solution (231 mL) and extracted with dichloromethane (2×250 mL). The combined organic phases were extracted with water (2×200 mL). The aqueous phase was evaporated to dryness under reduced pressure (water bath temperature 40° C.) to give (5S)-5-[(tert-butylsulfinyl)methyl]-5-methylimidazolidine-2,4-dione as white crystals (0.497 eq, 23.0 mmol, 5.34 g) in 50% yield as a 71:29 mixture of diastereoisomers (by comparison of $^1$H NMR integrals).

Major isomer: $^1$H NMR (499.914 MHz, DMSO-D6) δ 10.78 (s, 1H), 8.28 (s, 1H), 3.25 (d, J=14 Hz, 1H), 2.39 (d, J=14 Hz, 1H), 1.40 (s, 3H), 1.13 (s, 9H).

Minor isomer: $^1$H NMR (499.914 MHz, DMSO-D6) δ 10.78 (s, 1H), 8.07 (s, 1H), 2.85 (s, 2H), 1.38 (s, 3H), 1.14 (s, 9H).

FTIR of mixture (Neat) 3188, 3072, 2981, 2935, 2919, 1705, 1412, 1368, 1295, 1166, 1016, 877, 763, 599 cm$^{-1}$.

[(4S)-4-methyl-2,5-dioxoimidazolidin-4-yl]methanesulfonyl chloride via chlorination of (5S)-5-[(tert-butylsulfinyl)methyl]-5-methylimidazolidine-2,4-dione

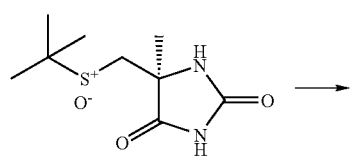

-continued

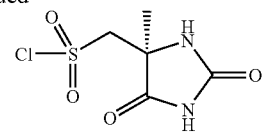

A stirred (350 rpm) solution of (5S)-5-[(tert-butylsulfinyl)methyl]-5-methylimidazolidine-2,4-dione (1.00 eq, 22.5 mmol, 5.22 g) in acetic acid (1.75 mol, 100 mL, 105 g) and water (555 mmol, 10.0 mL, 10.0 g) was cooled to 6° C. and purged with nitrogen. The nitrogen purge was stopped and chlorine gas (59.2 mmol, 4.2 g, 1.33 L at STP) was then bubbled through the mixture over a period of 25 min, maintaining the jacket temperature at 6° C. The temperature of the reaction mixture reached a maximum of 9.5° C. The end of reaction was determined by a persistent green colouration of the mixture and a fall in temperature from 9.1 to 7.8° C. over 1 min. The supply of chlorine was shut off and a nitrogen purge applied. HPLC analysis of the mixture at this point revealed complete conversion of the sulfoxide intermediates. The mixture was heated to 15° C., discharged from the vessel and concentrated under reduced pressure (bath temperature 45° C.). The residue was suspended in toluene (469 mmol, 50.0 mL, 43.3 g) and evaporated to low volume. Further toluene (469 mmol, 50.0 mL, 43.3 g) was added and the evaporation procedure repeated. The residue was triturated with iso-hexane (377 mmol, 50.0 mL, 32.5 g) and then collected by filtration. The resulting solid was washed with iso-hexane (151 mmol, 20.0 mL, 13.0 g), sucked dry on the filter and dried in vacuo for 24 h at 40° C. to give [(4S)-4-methyl-2,5-dioxoimidazolidin-4-yl]methanesulfonyl chloride as a white crystalline solid (0.874 eq, 19.6 mmol, 4.45 g) in 87% yield.

$^1$H NMR (399.98 MHz, THF-D8) δ 9.81 (s, 1H), 7.47 (s, 1H), 4.43 (d, J=14.4 Hz, 1H), 4.34 (d, J=14.6 Hz, 1H), 1.41 (s, 3H).

FTIR (Neat) 3191, 3073, 1704, 1408, 1377, 1369, 1287, 1166, 875, 762 cm$^{-1}$.

HPLC analysis (area %) indicated a purity of 99.69% containing [(4S)-4-methyl-2,5-dioxoimidazolidin-4-yl]methanesulfonic acid 0.31 area % by hplc.

The invention claimed is:

1. A process for the preparation of sulfonyl chloride derivatives of general formula (I)

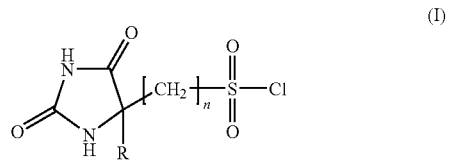

wherein

R represents C1 to 4 alkyl or C3 to 5 cycloalkyl; and n represents an integer 1 or 2;

which process involves reaction of a compound of formula (II)

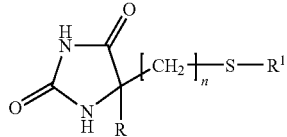

wherein

R$^1$ represents Bu$^t$, PhCH$_2$, Ph$_2$CH, Ph$_3$C or C1 to 6 alkanoyl; and

R and n are as defined in formula (I);

with hydrogen peroxide, followed by chlorination in an aqueous media.

2. A process according to claim 1 wherein the oxidation with hydrogen peroxide and the chlorination reaction are carried out as sequential steps within a single reaction vessel.

3. A process according to claim 1 wherein the reactions are carried out in aqueous acetic acid.

4. A process according to claim 1 wherein R$^1$ represents Bu$^t$.

5. A process according to claim 1 wherein R$^1$ represents PhCH$_2$.

6. A process according to claim 1 wherein n represents the integer 1.

7. A process according to claim 1 wherein R represents CH$_3$ or CH$_3$CH$_2$ or cyclopropyl.

8. A sulfoxide of general formula (IV)

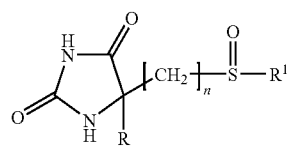

wherein R, R$^1$ and n are as defined in claim 1, useful as an intermediate in the synthesis of a sulfonyl chloride of general formula (I).

9. A sulfoxide according to claim 8 wherein R$^1$ represents CH$_3$ and R$^1$ represents Bu$^t$ or PhCH$_2$.

10. A sulfinic acid derivative of general formula (V)

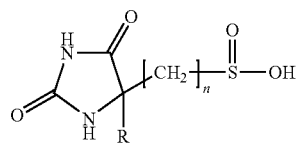

wherein R and n are as defined in claim 1, useful as an intermediate in the synthesis of a sulfonyl chloride of general formula (I).

11. A sulfinic acid derivative according to claim 10 wherein R represents CH$_3$.

* * * * *